US009643170B2

(12) United States Patent
Shin et al.

(10) Patent No.: US 9,643,170 B2
(45) Date of Patent: May 9, 2017

(54) LIGAND COMPOUND, CATALYST SYSTEM FOR OLEFIN OLIGOMERIZATION, AND METHOD FOR OLEFIN OLIGOMERIZATION USING THE SAME

(71) Applicant: LG CHEM, LTD., Seoul (KR)

(72) Inventors: Eun Ji Shin, Daejeon (KR); Yong Ho Lee, Daejeon (KR); Ki Soo Lee, Daejeon (KR); Seok Pil Sa, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/195,378

(22) Filed: Jun. 28, 2016

(65) Prior Publication Data

US 2016/0303552 A1 Oct. 20, 2016

Related U.S. Application Data

(62) Division of application No. 14/651,152, filed as application No. PCT/KR2014/008028 on Aug. 28, 2014, now Pat. No. 9,409,833.

(30) Foreign Application Priority Data

Nov. 19, 2013 (KR) ........................ 10-2013-0140872

(51) Int. Cl.
*D21H 19/46* (2006.01)
*B01J 35/00* (2006.01)
*B01J 31/00* (2006.01)
*B01J 31/18* (2006.01)
*C07C 2/32* (2006.01)
*B01J 31/14* (2006.01)
*C07F 9/46* (2006.01)
*C07F 9/572* (2006.01)
*C07F 9/655* (2006.01)

(52) U.S. Cl.
CPC ........... *B01J 31/188* (2013.01); *B01J 31/143* (2013.01); *B01J 31/146* (2013.01); *B01J 31/1845* (2013.01); *C07C 2/32* (2013.01); *C07F 9/46* (2013.01); *C07F 9/5727* (2013.01); *C07F 9/65515* (2013.01); *B01J 2231/20* (2013.01); *B01J 2531/62* (2013.01); *C07C 2531/14* (2013.01); *C07C 2531/18* (2013.01)

(58) Field of Classification Search
None
See application file for complete search history.

(56) References Cited

U.S. PATENT DOCUMENTS

| 8,076,523 B2 | 12/2011 | Bollmann et al. |
| 2008/0269443 A1 | 10/2008 | McConville et al. |
| 2011/0015061 A1 | 1/2011 | Gao et al. |
| 2011/0282016 A1 | 11/2011 | Carter et al. |
| 2012/0172645 A1 | 7/2012 | Sydora |

FOREIGN PATENT DOCUMENTS

| CN | 101351424 A | 1/2009 |
| CN | 101935367 A | 1/2011 |
| EP | 2520366 A1 | 11/2012 |
| GB | 1544778 | 4/1979 |
| JP | 5-310737 A | 11/1993 |
| JP | 2000-507604 A | 6/2000 |
| JP | 2008-533030 A | 8/2008 |
| JP | 2008-533047 A | 8/2008 |
| JP | 2009-516672 A | 4/2009 |
| KR | 10-2008-0080570 A | 9/2008 |
| KR | 10-2012-0098711 A | 9/2012 |
| KR | 10-2012-0138309 A | 12/2012 |
| KR | 10-1241656 B1 | 3/2013 |
| KR | 10-2013-0105126 A | 9/2013 |
| WO | 02/065526 A1 | 8/2002 |
| WO | 2008/014139 A2 | 1/2008 |
| WO | 2012/097146 A1 | 7/2012 |

OTHER PUBLICATIONS

Anthea Carter et al.: "High activity ethylene trimerisation catalysts based on diphosphine ligands", ChemComm., Feb. 8, 2002, pp. 858-859.
Kevin Blann et al.: "Ethylene tetramerisation: Subtle effects exhibited by N-substituted diphosphinoamine ligands", ScienceDirect, Journal of Catalysis 249, (2007), pp. 244-249.
Sven Kuhlmann et al.: "N-substituted diphosphinoamines: Toward rational ligand design for the efficient tetramerization of ethylene", ScienceDirect, Journal of Catalysis 245, (2007), pp. 279-284.

*Primary Examiner* — Yun Qian
(74) *Attorney, Agent, or Firm* — Dentons US LLP

(57) ABSTRACT

This disclosure relates to a novel ligand compound that can oligomerize ethylene with high catalyst activity and selectivity, a catalyst system for olefin oligomerization including the same, and a method for olefin oligomerization using the same.

4 Claims, No Drawings

LIGAND COMPOUND, CATALYST SYSTEM FOR OLEFIN OLIGOMERIZATION, AND METHOD FOR OLEFIN OLIGOMERIZATION USING THE SAME

RELATED APPLICATIONS

This application is a divisional application of U.S. patent application Ser. No. 14/651,152, filed Jun. 10, 2015, which application is a National Stage Entry of International Application No. PCT/KR2014/008028, filed Aug. 28, 2014, and claims the benefit of and priority to Korean Application No. 10-2013-0140872, filed Nov. 19, 2013, all of which are incorporated herein by reference in their entirety for all purposes as if fully set forth herein.

TECHNICAL FIELD

The present invention relates to a ligand compound, a catalyst system for olefin oligomerization, and a method for olefin oligomerization using the same.

BACKGROUND OF ART

Linear alpha-olefins are important materials used as comonomers, cleaners, lubricants, plasticizers, and the like, and are widely used industrially. Particularly, 1-hexene and 1-octene are used as comonomers for controlling the density of polyethylene when preparing linear low density polyethylene (LLDPE).

In the conventional preparation process of LLDPE, copolymerization with comonomers such as alpha-olefins, for example, 1-hexene and 1-octene, is conducted so that a branch may be formed in the polymer backbone together with ethylene to control the density.

Thus, in order to prepare LLDPE with high comonomer content, there is a problem in that the cost of comonomers accounts for a great part of the production cost. Various attempts have been made in order to overcome this problem.

Since alpha-olefins have different application fields or market fields according to the kind, technologies capable of selectively producing specific olefins is commercially important, and recently, many studies have progressed on chromium catalyst technology for preparing 1-hexene or 1-octene with high selectivity through selective ethylene oligomerization.

Existing commercial methods for preparing 1-hexene or 1-octene include the SHOP process of Shell Chemical, the Ziegler process of Chevron Philips, and the like, which may be used to produce a wide distribution of alpha-olefins ranging from C4-20.

As a trimerization catalyst of ethylene, a chromium-based catalyst using a ligand of general formula (R1)(R2)X—Y—X(R3)(R4) has been suggested. In the formula, X is phosphorus, arsenic, or antimony, Y is a linking group such as —N(R5)-, and at least one of R1, R2, R3, and R4 has a polar or electron accepting substituent.

A representative example of such ligands is (o-ethylphenyl)$_2$PN(Me)P(o-ethylphenyl)$_2$, which is a compound wherein at least one of R1, R2, R3, and R4 does not have a polar substituent (*Chem. Commun.*, 2002, 858).

However, there is continued demand for development of ligands that have continuously continued oligomerization activity and high selectivity when preparing 1-octene or 1-hexene.

PRIOR ART DOCUMENT

Non-Patent Documents

1. *Chem. Commun.*, 2002, 858

DETAILED DESCRIPTION OF THE INVENTION

Technical Problem

It is the object of the invention to provide a ligand compound that can oligomerize ethylene with high catalytic activity and selectivity, a catalyst system for olefin oligomerization including the same, and a method for olefin oligomerization using the same.

Technical Solution

A ligand compound according to one aspect of the invention may be represented by the following Chemical Formula 1.

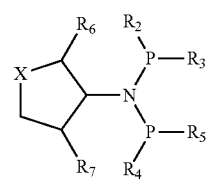

[Chemical Formula 1]

In Chemical Formula 1,
X is $R_1$—N, O, or S,
$R_1$ is a C1-20 alkyl group, a C6-40 aryl group, a C3-30 heteroaryl group, an arylalkyl group, optionally containing at least one heteroatom selected from N, O, F, S, and P, or hydrogen,
$R_2$ to $R_5$ are independently a C6-40 aryl group, and
$R_6$ and $R_7$ are H or a C1-20 alkyl group.

A catalyst system for olefin oligomerization according to another aspect of the invention may include a ligand compound represented by the following Chemical Formula 1, a chromium source, and a cocatalyst.

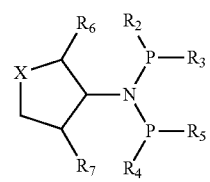

[Chemical Formula 1]

In Chemical Formula 1,
X is $R_1$—N, O, or S,
$R_1$ is a C1-20 alkyl group, a C6-40 aryl group, a C3-30 heteroaryl group, an arylalkyl group, optionally containing at least one heteroatom selected from N, O, F, S, and P, or hydrogen,
$R_2$ to $R_5$ are independently a C6-40 aryl group, and
$R_6$ and $R_7$ are H or a C1-20 alkyl group.

A method for olefin oligomerization according to yet another aspect may include the step of oligomerizing olefins in the presence of a catalyst system for olefin oligomerization including a ligand compound represented by the following Chemical Formula 1, a chromium source, and a cocatalyst.

[Chemical Formula 1]

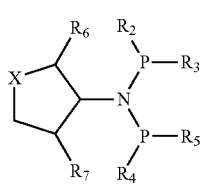

In Chemical Formula 1,

X is $R_1$—N, O, or S, $R_1$ is a C1-20 alkyl group, a C6-40 aryl group, a C3-30 heteroaryl group, an arylalkyl group, optionally containing at least one heteroatom selected from N, O, F, S, and P, or hydrogen, $R_2$ to $R_5$ are independently a C6-40 aryl group, and $R_6$ and $R_7$ are H or a C1-20 alkyl group.

Advantageous Effects

By using the catalyst system including the ligand compound according to the present invention, ethylene can be oligomerized with high selectivity compared to the existing catalyst system.

DETAILED DESCRIPTION OF THE EMBODIMENTS

Although various modifications may be made in the present invention, and the present invention may have various embodiments, specific embodiments will be explained in detail in the specification. However, it is to be understood that the present invention is not limited to specific embodiments, and covers all modifications, equivalents, and alternatives falling within the spirit and the scope of the invention. If it is judged that detailed explanations regarding related known technologies may obscure the subject matter of the invention, the detailed explanations will be omitted.

The present invention provides a ligand compound represented by the following Chemical Formula 1.

[Chemical Formula 1]

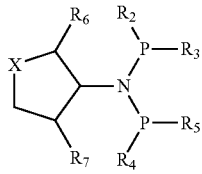

In Chemical Formula 1,

X is $R_1$—N, O, or S, $R_1$ is a C1-20 alkyl group, a C6-40 aryl group, a C3-30 heteroaryl group, an arylalkyl group, optionally containing at least one heteroatom selected from N, O, F, S, and P, or hydrogen, $R_2$ to $R_5$ are independently a C6-40 aryl group, and $R_6$ and $R_7$ are H or a C1-20 alkyl group.

According to another aspect of the invention, a catalyst system including the ligand compound represented by Chemical Formula 1, a chromium source, and a cocatalyst is provided.

According to yet another aspect of the invention, a method for olefin oligomerization including the step of oligomerizing olefins in the presence of a catalyst system for olefin oligomerization including a ligand compound represented by Chemical Formula 1, a chromium source, and a cocatalyst is provided.

The catalyst for olefin oligomerization of the prior art has a problem in that it does not have high oligomerization activity and high selectivity. Thus, the inventors confirmed through experiments that if a catalyst system including the novel ligand compound is used, high oligomerization activity and high selectivity may be consistently maintained in olefin oligomerization, and completed the invention.

Hereinafter, a ligand compound, a catalyst system for olefin oligomerization, and a method for olefin oligomerization using the same according to the present invention will be explained detail.

Ligand Compound

The ligand compound of the present invention may be represented by the following Chemical Formula 1.

[Chemical Formula 1]

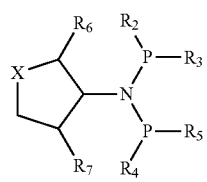

In Chemical Formula 1,

X is $R_1$—N, O, or S, $R_1$ is a C1-20 alkyl group, a C6-40 aryl group, a C3-30 heteroaryl group, an arylalkyl group, optionally containing at least one heteroatom selected from N, O, F, S, and P, or hydrogen, $R_2$ to $R_5$ are independently a C6-40 aryl group, and $R_6$ and $R_7$ are H or a C1-20 alkyl group.

More specifically, according to one embodiment of the invention, examples of the ligand compound represented by Chemical Formula 1 may be represented by one of the following structural formulae, but are not limited thereto. The following compounds may be prepared by a common method for preparing a ligand, and will be explained in more detail in examples below.

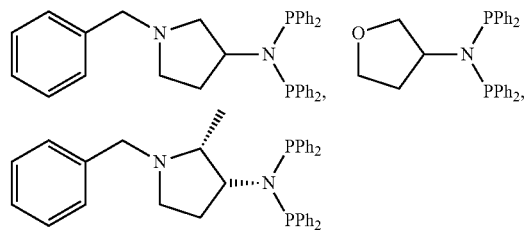

The compound represented by Chemical Formula 1 may be synthesized by the following method, but is not limited thereto.

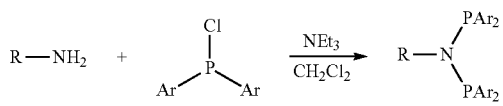

Catalyst System for Olefin Oligomerization

The catalyst system for olefin oligomerization according to the present invention may include a ligand compound represented by the following Chemical Formula 1; a chromium source; and a cocatalyst.

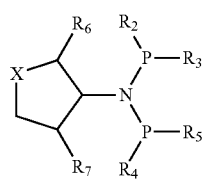

[Chemical Formula 1]

In Chemical Formula 1,

X is $R_1$—N, O, or S, $R_1$ is a C1-20 alkyl group, a C6-40 aryl group, a C3-30 heteroaryl group, an arylalkyl group, optionally containing at least one heteroatom selected from N, O, F, S, and P, or hydrogen, $R_2$ to $R_5$ are independently a C6-40 aryl group, and $R_6$ and $R_7$ are H or a C1-20 alkyl group.

In the catalysts system for olefin oligomerization of the present invention, a "catalyst system" means that the compound represented by Chemical Formula 1 and a cocatalyst are simultaneously or sequentially added in any suitable solvent in the presence/absence of monomers, and can be obtained as an active catalyst composition.

According to one embodiment of the invention, the chromium source may be chromium or a chromium precursor. Specific examples of the chromium or chromium precursor may be chromium (III) acetylacetonate, tris(tetrahydrofuran)chromium trichloride, or chromium (III)-2-ethylhexanoate, but is not limited thereto.

The catalyst system for olefin oligomerization includes a cocatalyst. The cocatalyst is an organic metal compound containing a Group 13 metal, and in general, is not specifically limited as long as it can be used for oligomerization of an olefin in the presence of a transition metal catalyst.

Specifically, the cocatalyst may be at least one selected from the group consisting of compounds represented by the following Chemical Formulae 2 to 4, but is not limited thereto.

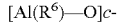

[Chemical Formula 2]

In Chemical Formula 2, $R^6$'s are identical to or different from each other, and are independently a halogen radical, a C1-20 hydrocarbyl radical, or a C1-20 hydrocarbyl radical substituted with a halogen, and c is an integer equal to or greater than 2.

[Chemical Formula 3]

In Chemical Formula 3,

D is aluminum or boron, and $R^7$'s are independently a C1-20 hydrocarbyl or a C1-20 hydrocarbyl substituted with a halogen.

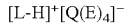

[Chemical Formula 4]

In Chemical Formula 4,

L is neutral Lewis base, [L-H]$^+$ is a Bronsted acid, Q is boron or aluminum in a +3 oxidation state, and E's are independently a C6-20 aryl group or a C1-20 alkyl group, at least one hydrogen of which is unsubstituted or substituted with a halogen, a C1-20 hydrocarbyl, an alkoxy functional group, or a phenoxy functional group.

Examples of the compound represented by Chemical Formula 2 may include methylaluminoxane (MAO), ethylaluminoxane, isobutylaluminoxane, butylaluminoxane, and the like.

Examples of the alkyl metal compound represented by Chemical Formula 3 may include trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum tri-p-tolylaluminum, dimethylaluminummethoxide, dimethylaluminumethoxide, trimethylboron, triethylboron, triisobutylboron, tripropylboron, tributylboron, and the like.

Examples of the compound represented by Chemical Formula 4 may include triethylammoniumtetraphenylboron, tributylammoniumtetraphenylboron, trimethylammoniumtetraphenylboron, tripropylammoniumtetraphenylboron, trimethylammoniumtetra(p-tolyl)boron, tripropylammoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl)boron, trimethylammoniumtetra(p-trifluoromethylphenyl)boron, tributylammoniumtetrapentafluorophenylboron, N,N-diethylaniliniumtetraphenylboron, N,N-diethylaniliniumtetraphenylboron, N,N-diethylaniliniumtetrapentafluorophenylboron, diethylammoniumtetrapentafluorophenylboron, triphenylphosphoniumtetraphenylboron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra(p-trifluoromethylphenyl)aluminum, tributylammoniumtetrapentafluorophenylaluminum, N,N-diethylaniliniumtetraphenylaluminum, N,N-diethylaniliniumtetrapentafluorophenylaluminum, diethylammoniumtetrapentafluorophenylaluminum, triphenylphosphoniumtetraphenylaluminum, triphenylcarboniumtetraphenylboron, triphenylcarboniumtetra(p-trifluoromethylphenyl)boron, triphenylcarboniumtetrapentafluorophenylboron, and the like.

Preferably, an alumoxane may be used, and more preferably, an alkylalumoxane such as methylalumoxane (MAO) may be used.

According to one embodiment of the invention, the catalyst system for olefin oligomerization may include the ligand compound represented by Chemical Formula 1, a chromium source, and a cocatalyst. Herein, in order to increase selectivity to linear alpha olefins and increase oligomerization activity, the mole ratio of the ligand compound:chromium source:cocatalyst may be about 1:1:1 to about 10:1:10,000, preferably about 1:1:100 to about 5:1:3,000, but is not limited thereto.

In a catalyst system including the ligand compound represented by Chemical Formula 1, a chromium source, and a cocatalyst, the three components of the catalyst system may be added simultaneously or sequentially and in any order in any suitable solvent in the presence or absence of monomers and obtained as an active catalyst. The suitable solvent may include heptanes, toluene, 1-hexene, diethylether, tetrahydrofuran, acetonitrile, dichloromethane, chloroform, chlorobenzene, methanol, acetone, and the like, but is not limited thereto.

By using the catalyst system according to the present invention, a method for olefin oligomerization with improved reaction activity and selectivity may be provided.

Method for Olefin Oligomerization

The method for olefin oligomerization according to the present invention may include the step of oligomerizing olefins in the presence of a catalyst system for olefin oligomerization including a ligand compound represented by the following Chemical Formula 1, a chromium source, and a cocatalyst.

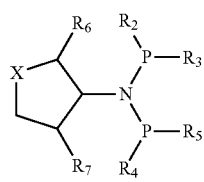

[Chemical Formula 1]

In Chemical Formula 1,

X is $R_1$—N, O, or S, $R_1$ is a C1-20 alkyl group, a C6-40 aryl group, a C3-30 heteroaryl group, an arylalkyl group, optionally containing at least one heteroatom selected from N, O, F, S, and P, or hydrogen, $R_2$ to $R_5$ are independently a C6-40 aryl group, and $R_6$ and $R_7$ are H or a C1-20 alkyl group.

According to one embodiment of the invention, an olefin oligomer may be prepared by a homogeneous liquid phase reaction, a slurry reaction wherein a part of or the whole catalyst system is not dissolved, a two-phase liquid/liquid reaction, or a bulk phase reaction wherein product olefin acts as a main medium, or a gas phase reaction, in the presence or absence of in inert solvent using the catalyst system according to above-explained embodiment and a common device and contact technology, but the homogeneous liquid phase reaction is preferable.

The olefin oligomerization may be conducted in any inert solvent that does not react with a catalyst compound and an activator. Suitable inert solvents may include benzene, toluene, xylene, cumene, heptanes, cyclohexane, methylcyclohexane, methylcyclopentane, hexane, pentane, butane, isobutene, and the like, but are not limited thereto. Herein, according to one embodiment of the invention, the solvent may be treated with a small amount of alkyl aluminum to remove a small amount of water or air and the like that act as a catalyst poison.

According to one embodiment of the invention, the olefin oligomerization may be conducted at a temperature of about 5 to about 200° C., preferably about 30 to about 150° C.

According to one embodiment of the invention, the olefin oligomerization may be conducted at a pressure of about 1 to about 300 bar, preferably about 2 to about 150 bar.

When conducting olefin oligomerization using a catalyst system, if the above-explained compound or a catalyst system including the same according to the present invention is used, high selectivity to 1-hexene and 1-octene may be achieved.

Hereinafter, preferable examples of the invention will be explained in detail. However, these examples are only to illustrate the invention, and the scope of the invention is not limited thereto.

Synthesis of Ligand Compound

Synthesis Example

All the reactions were progressed under argon using the Schlenk technique or a glove box. The synthesized ligand was analyzed by $^1$H (500 MHz) and $^{31}$P (202 MHz) NMR spectra using a Varian 500 MHz spectrometer. The shift was expressed in ppm, downfield from TMS with the residual solvent peak as reference. A phosphorous probe was calibrated with aqueous $H_3PO_4$. Under Ar, amine (10 mmol) and triethylamine (3~10 equiv. to amine) were dissolved in dichloromethane (80 mL). While the flask was immersed in a water bath, chlorodiphenylphosphine (20 mmol) was slowly added thereto, and agitated overnight. After evaporation of the solvent under vacuum, other solvents (diethyl ether, tetrahydrofuran, or hexane) were added thereto and sufficiently agitated, and triethylammonium chloride salt was removed with an air-free glass filter. The solvent was removed from the filtrate to obtain a product. The starting amines for preparing the ligands used in examples and comparative examples are shown in the following Table 1.

TABLE 1

| Synthesis Example | Starting amine | Ligand |
|---|---|---|
| Synthesis Example 1 | 1-Benzyl-3-aminopyrrolidine | |
| Synthesis Example 2 | 3-amino-tetrahydrofuran HCl | |
| Synthesis Example 3 | cis-3-Amino-1-benzyl-2-methylpyrrolidine | |
| Synthesis Example 4 | 2-aminopropane | |

Ethylene Oligomerization

Example 1

Under argon gas, Cr(acac)$_3$ (17.5 mg, 0.05 mmol) and the ligand 1 (0.1 mmol) prepared according to Synthesis Example 1 were put in a flask, 10 ml of toluene was added, and the mixture was agitated to prepared a 5 mM solution.

A magnetic stir bar was put into a 100 mL Parr reactor and assembled, and then the inside was placed under vacuum (for at least 2 hours). After replacing the inside with Ar, 46 mL of cyclohexane and 2 mL of MAO (10 wt % toluene solution, Al/Cr=300) were injected. 2 mL (10 μmol) of a 5 mM catalyst solution (toluene) was injected into the reactor. The reactor was immersed in an oil bath heated to 45° C., and connected with an ethylene supply. The pressure of ethylene was adjusted to 45 bar, and agitation began at 600 rpm. After 15 minutes of reaction, the ethylene was cut off, and the reactor was taken out and cooled with a dry ice/acetone bath. After venting, the reactor was opened and 0.5 mL of nonane (GC internal standard) was added thereto. About 2 mL of the liquid part was taken and quenched with water, and the organic part was filtered with a PTFE syringe filter to prepare a GC sample. The distribution of the liquid product was analyzed with GC. To the remaining reaction solution, 300 mL of ethanol/HCl (10 vol %) was added, and the solution was agitated and filtered to obtain a polymer. The polymer was dried overnight in a vacuum oven at 65° C.

Example 2

Ethylene oligomerization was conducted by the same method as Example 1, except that the ligand prepared according to Synthesis Example 2 was used.

Example 3

Ethylene oligomerization was conducted by the same method as Example 1, except that the ligand prepared according to Synthesis Example 3 was used.

Comparative Example 1

Ethylene oligomerization was conducted by the same method as Example 1, except that the ligand prepared according to Synthesis Example 4 was used, and methylcyclohexane was used as a reaction solvent.

The results of Examples 1 to 3 and Comparative Example 1 are summarized in the following Table 2.

TABLE 2

| | Activity (kg/molCr/hr) | 1-$C_6$ (wt %) | 1-$C_8$ (wt %) | Sum (wt %) |
|---|---|---|---|---|
| Comparative Example | 980 | 16.3 | 52.5 | 68.8 |
| Example 1 | 844 | 15.1 | 61.0 | 76.1 |
| Example 2 | 1410 | 20.5 | 51.2 | 71.7 |
| Example 3 | 380 | 30.6 | 54.1 | 84.7 |

As shown in Table 2, in the examples, selectivity to 1-hexene and 1-octene was remarkably improved compared to the comparative example.

Although specific parts of the invention have been described in detail, it would be obvious to one of ordinary knowledge in the art that such specific technologies are no more than preferable embodiments, and the scope of the invention is not limited thereto. Thus, the scope of the invention is defined by the attached claims and equivalents thereof.

The invention claimed is:

1. A catalyst system for olefin oligomerization, comprising:
   a ligand compound represented by the following Chemical Formula 1;
   a chromium source selected from the group consisting of chromium (III) acetylacetonate, tris(tetrahydrofuran) chromium trichloride, and chromium (III)-2-ethylhexanoate; and
   a cocatalyst:

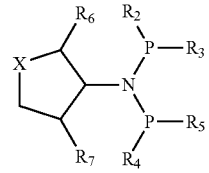

[Chemical Formula 1]

wherein, in chemical Formula 1,
X is $R_1$—N, O, or S,
$R_1$ is hydrogen, a C1-20 alkyl group, a C6-40 aryl group, a C3-30 heteroaryl group, or a C3-30 arylalkyl group, wherein the alkyl group, the aryl group, the heteroaryl group and the arylalkyl group optionally contain at least one heteroatom selected from N, O, F, S, and P,
$R_2$ to $R_1$ are independently a C6-40 aryl group, and
$R_6$ and $R_7$ are H or a C1-C20 alkyl group.

2. The catalyst system according to claim 1, wherein the ligand compound represented by Chemical Formula 1 is selected from the group consisting of

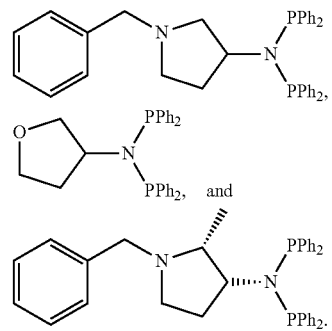

3. The catalyst system according to claim 1, wherein the cocatalyst is at least one selected from the group consisting of compounds represented by the following Chemical Formulae 2 to 4:

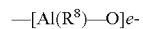  [Chemical Formula 2]

wherein, in Chemical Formula 2, $R^8$'s are identical to or different from each other, and are independently are a halogen radical, a C1-20 hydrocarbyl radical, or a C1-C20 hydrocarbyl radical substituted with a halogen, and c is an integer equal to or greater than 2,

  [Chemical Formula 3]

wherein, in Chemical Formula 3,
D is aluminum or boron, $R^9$'s are independently a C1-C20 hydrocarbyl or a C1-20 hydrocarbyl substituted with a halogen, and

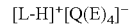  [Chemical Formula 4]

wherein, in Chemical Formula 4,
L is a neutral Lewis base, $[L-H]^+$ is a Bronsted acid, Q is boron or aluminum in a +3 oxidation state, E's are independently a C6-20 aryl group or a C1-20 alkyl group, at least one hydrogen of which is substituted or substituted with a halogen, a C1-20 hydrocarbyl, an alkoxy functional group, or a phenoxy functional group.

4. The catalyst system according to claim 1, wherein the olefin is ethylene.

* * * * *